(12) United States Patent
Zeimantz

(10) Patent No.: US 6,654,114 B2
(45) Date of Patent: *Nov. 25, 2003

(54) INTEGRATED CIRCUIT DEFECT REVIEW AND CLASSIFICATION PROCESS

(75) Inventor: Lisa R. Zeimantz, Boise, ID (US)

(73) Assignee: Micron Technology, Inc., Boise, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 10/213,129

(22) Filed: Aug. 5, 2002

(65) Prior Publication Data
US 2002/0191181 A1 Dec. 19, 2002

Related U.S. Application Data

(63) Continuation of application No. 09/941,253, filed on Aug. 28, 2001, now Pat. No. 6,441,897, which is a continuation of application No. 09/839,777, filed on Apr. 20, 2001, now Pat. No. 6,373,566, which is a continuation of application No. 09/537,030, filed on Mar. 28, 2000, now Pat. No. 6,259,520, which is a continuation of application No. 08/790,999, filed on Jan. 30, 1997, now Pat. No. 6,072,574.

(51) Int. Cl.$^7$ .............................................. G01N 21/00
(52) U.S. Cl. ................................ 356/237.4; 356/237.5; 356/394; 250/310
(58) Field of Search ......................... 356/237.1, 237.2, 356/237.3, 237.4, 237.5, 239.1, 239.3, 239.7, 239.8, 394, 429–431; 250/307, 310

(56) References Cited

U.S. PATENT DOCUMENTS

| 4,209,257 | A | 6/1980 | Uchiyama et al. |
| 4,376,583 | A | 3/1983 | Alford et al. |
| 4,778,745 | A | 10/1988 | Leung |
| 4,791,586 | A | 12/1988 | Maeda et al. |
| 5,103,166 | A | 4/1992 | Jeon et al. |
| 5,127,726 | A | 7/1992 | Moran |
| 5,240,866 | A | 8/1993 | Friedman et al. |
| 5,294,812 | A | 3/1994 | Hashimoto et al. |
| 5,301,143 | A | 4/1994 | Ohri et al. |
| 5,539,752 | A | 7/1996 | Berezin et al. |
| 5,544,256 | A | 8/1996 | Brecher et al. |
| 5,550,372 | A | 8/1996 | Yasue |
| 6,072,574 | A | 6/2000 | Zeimantz |
| 6,259,520 | B1 | 7/2001 | Zeimantz |
| 6,373,566 | B2 | 4/2002 | Zeimantz |
| 6,441,897 | B1 * | 8/2002 | Zeimantz ................. 356/237.4 |

* cited by examiner

Primary Examiner—Hoa Q. Pham
(74) Attorney, Agent, or Firm—TraskBritt

(57) ABSTRACT

The present invention relates to circuit defect detection, classification, and review in the wafer stage of the integrated circuit semiconductor device manufacturing process. The method of processing integrated circuit semiconductor dice on a wafer in a manufacturing process for dice comprises the steps of visually inspecting the dice on the wafer to determine defects thereon, summarizing the number, types, and ranges of sizes of the defects of the dice on the wafer, and determining if the wafer is acceptable to proceed in the manufacturing process.

21 Claims, 8 Drawing Sheets

SCANNING ELECTRON MICROSCOPE
DEFECT REVIEW SHEET
SUMMARY

PART TYPE:
LOT NUMBER:
WAFER ID:
STEP:

TEST #:
KLA #:
DATE:
TIME IN/OUT:
KLA OPERATOR ID:

SLOT:
DEFECT CNT:
REVIEW OPERATOR ID:

SEM PICTURE REQUIRED ☐ YES ☐ NO
SURFACE DEFECT RANGE (MICRONS)

| 0-0.5 (MICRONS) | | | 0.5-1 (MICRONS) | | | 1-2 (MICRONS) | | | 2-4 (MICRONS) | | | >4 (MICRONS) | | |
|---|---|---|---|---|---|---|---|---|---|---|---|---|---|---|
| ID | CL | P | ID | CL | P | ID | CL | P | ID | CL | P | ID | CL | P |
| 329 | 3 | | 402 | 2 | | | | | 2128 | 2 | | 2197 | 1 | 8 |
| | | | 408 | 2 | | | | | | | | | | |
| | | | c 4 437 | 2 | | | | | | | | | | |
| | | | c 4 440 | 2 | | | | | | | | | | |
| | | | 623 | 2 | | | | | | | | | | |
| | | | c 25 2045 | 2 | | | | | | | | | | |
| | | | c 25 2079 | 2 | | | | | | | | | | |
| | | | 2167 | 2 | | | | | | | | | | |
| | | | 2198 | 1 | | | | | | | | | | |

— 104

| DEFECT TYPE | DESCRIPTION OF TYPE DEFECT | TOTAL |
|---|---|---|
| 1 | PEELING BOND PADS | 2 |
| 2 | SCUMMING | 9 |
| 3 | PARTICLE | 1 |
| 4 | | |
| 5 | | |
| 6 | CANNOT FIND | |

INTEGRATED CIRCUIT DEFECT REVIEW AND CLASSIFICATION PROCESS

CROSS-REFERENCE TO RELATED APPLICATIONS

This application is a continuation of application Ser. No. 09/941,253, filed Aug. 28, 2001, now U.S. Pat. No. 6,441,897 B1, issued Aug. 27, 2002, which is a continuation of application Ser. No. 09/839,777, filed Apr. 20, 2001, now U.S. Pat. No. 6,373,566 B2, issued Apr. 16, 2002, which is a continuation of application Ser. No. 09/537,030, filed Mar. 28, 2000, now U.S. Pat. No. 6,259,520 B1, issued Jul. 10, 2001, which is a continuation of application Ser. No. 08/790,999, filed Jan. 30, 1997, now U.S. Pat. No. 6,072,574, issued Jun. 6, 2000.

BACKGROUND OF THE INVENTION

1. Field of the Invention

The present invention relates in general to integrated circuit semiconductor device manufacturing. More specifically, the present invention relates to integrated circuit defect detection, classification, and review in the wafer stage of the integrated circuit semiconductor device manufacturing process.

2. State of the Art

Integrated circuit semiconductor devices (IC's) are small electronic circuits formed on the surface of a wafer of semiconductor material, such as silicon, in a manufacturing process referred to as "fabrication." Once fabricated while in wafer form, IC's are electronically probed to evaluate a variety of their electronic characteristics, subsequently cut from the wafer on which they were formed into discrete IC dice or "chips," and then further tested and assembled for customer use through various well-known individual die IC testing and packaging techniques, including lead frame packaging, Chip-On-Board (COB) packaging, and flip-chip packaging.

Before being shipped to customers, packaged IC's are generally tested to ensure various functions thereof. Testing typically involves a variety of known test steps, such as pre-grade, burn-in, and final, which test IC's for defects and functionality and grade IC's for speed. As shown in FIG. 1, IC's that pass the described testing are generally shipped to customers, while IC's that fail the testing are typically rejected.

The testing standards for a particular IC product are sometimes relaxed as the product "matures" such that IC's previously rejected under strict testing standards may pass the relaxed testing standards. Consequently, reject bins containing previously rejected IC's are sometimes "culled" for IC's that are shippable under relaxed testing standards by testing the rejected IC's again using the relaxed testing standards. Unfortunately, while this "culling" process does retrieve shippable IC's from reject bins, it makes inefficient use of expensive and often limited testing resources by diverting those resources away from testing untested IC's in order to retest previously rejected IC's.

Similarly, as shown in FIG. 2, all the IC's from the wafers in a wafer lot typically undergo enhanced reliability testing that is more extensive and strict than normal testing when any of the wafers in the lot are deemed to be unreliable because of fabrication or other process errors. Since a wafer lot typically consists of fifty or more wafers, many of the IC's that undergo the enhanced reliability testing do not require it because they come from wafers that are not deemed unreliable. Performing enhanced reliability testing on IC's that do not need it is inefficient because such testing is typically more time-consuming and uses more resources than normal testing.

Likewise, as shown in FIG. 3, a new or special "recipe" for fabricating IC's on wafers is sometimes tested by fabricating some wafers from a wafer lot using the special recipe and other wafers from the wafer lot using a control recipe. IC's from the wafers then typically undergo separate assembly and test procedures so that the test results of IC's fabricated using the special recipe are not mixed with the test results of IC's fabricated using the control recipe, and vice versa. Test reports from the separate test procedures are then used to evaluate the special recipe and to determine whether the IC's are to be shipped to customers, reworked, repaired, retested, or rejected. Unfortunately, because the IC's undergo separate test and assembly procedures, undesirable variables, such as differences in assembly and test equipment, are introduced into the testing of the special recipe. It would be desirable, instead, to be able to assemble and test the IC's using the same assembly and test procedures, and to then sort the IC's and their test results into those IC's fabricated using the special recipe and those IC's fabricated using the control recipe.

As described above, IC's are typically tested for various characteristics before being shipped to customers. For example, as shown in FIG. 4, IC's may be graded in test for speed and placed in various bins according to their speed. If a customer subsequently requests a more stringent speed grade, IC's in one of the bins are retested and thereby sorted into IC's that meet the more stringent speed grade and those that do not. While this conventional process sorts the IC's into separate speed grades, it makes inefficient use of expensive and often limited testing resources by diverting those resources away from testing untested IC's in order to retest previously tested IC's.

As described in U.S. Pat. Nos. 5,301,143, 5,294,812, and 5,103,166, some methods have been devised to electronically identify individual IC's. Such methods take place "off" the manufacturing line and involve the use of electrically retrievable ID codes, such as so-called "fuse-ID's," programmed into individual IC's to identify the IC's. The programming of a fuse-ID typically involves selectively blowing an arrangement of fuses and anti-fuses in an IC so that when the fuses or anti-fuses are accessed, they output a selected ID code. Unfortunately, none of these methods addresses the problem of identifying IC's on a manufacturing line which will probably fail during subsequent testing and processing to help minimize the use of processing resources and time.

As can be readily seen, since IC's which are ultimately sold to customers involve extensive testing and subsequent packaging of the IC device, it becomes important to identify potentially defective IC's as early as possible in the manufacturing process to help eliminate associated testing, processing, and packaging costs therewith. In particular, if defects in IC's can be identified early in the manufacturing process before any testing occurs while the IC's are still in wafer form, it is very beneficial in the manufacturing process, particularly, if the defects in the IC's can be identified while the IC's are still in wafer form before any substantial testing has been done of the IC's on the wafer. It is also beneficial to identify and classify the defects of the IC's while in wafer form to determine if the wafer should proceed in the various processes of test, manufacture, and packaging with other wafers in the same manufacturing production lot when the inclusion of a wafer having IC's with numerous defects therein may cause the unnecessary testing of other IC's from other wafers in the manufacturing production lot.

SUMMARY OF THE INVENTION

The present invention relates to circuit defect detection, classification, and review in the wafer stage of the integrated circuit semiconductor device manufacturing process. The method of processing integrated circuit semiconductor dice on a wafer in a manufacturing process for dice comprises the steps of visually inspecting the dice on the wafer to determine defects thereon, summarizing the number, types, and ranges of sizes of the defects of the dice on the wafer, and determining if the wafer is acceptable to proceed in the manufacturing process.

BRIEF DESCRIPTION OF THE SEVERAL VIEWS OF THE DRAWINGS

FIG. 6 is a tabular summary of defect type, defect description, and total number of defects of preselected dice of a wafer according to the present invention.

The present invention will be more fully understood when the drawings are taken in conjunction with the detailed description of the invention hereinafter.

DETAILED DESCRIPTION OF THE INVENTION

Figure 1:
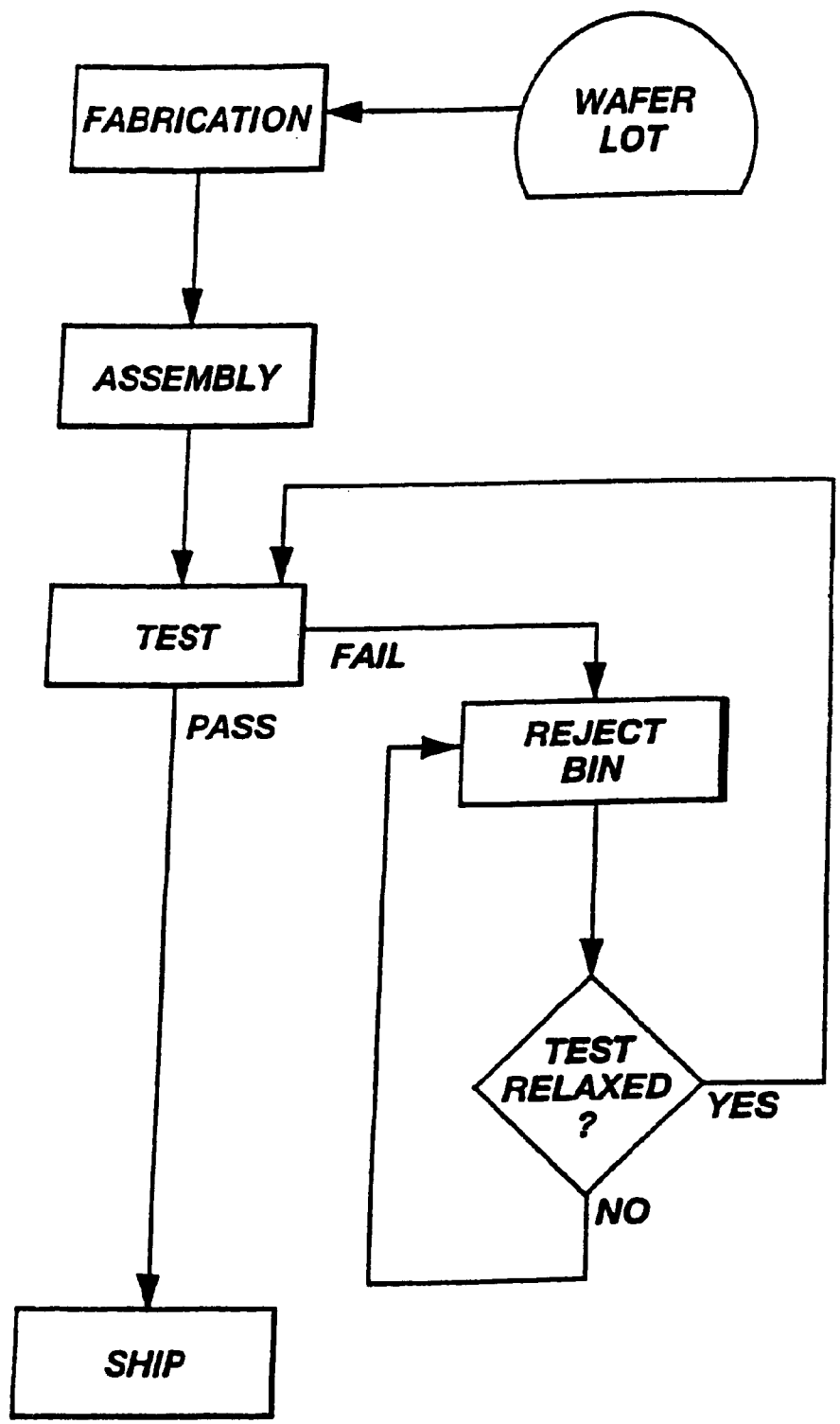
FIG. 1 is a flow diagram illustrating a conventional procedure in an integrated circuit manufacturing process for culling shippable IC's from a reject bin.
Figure 2:
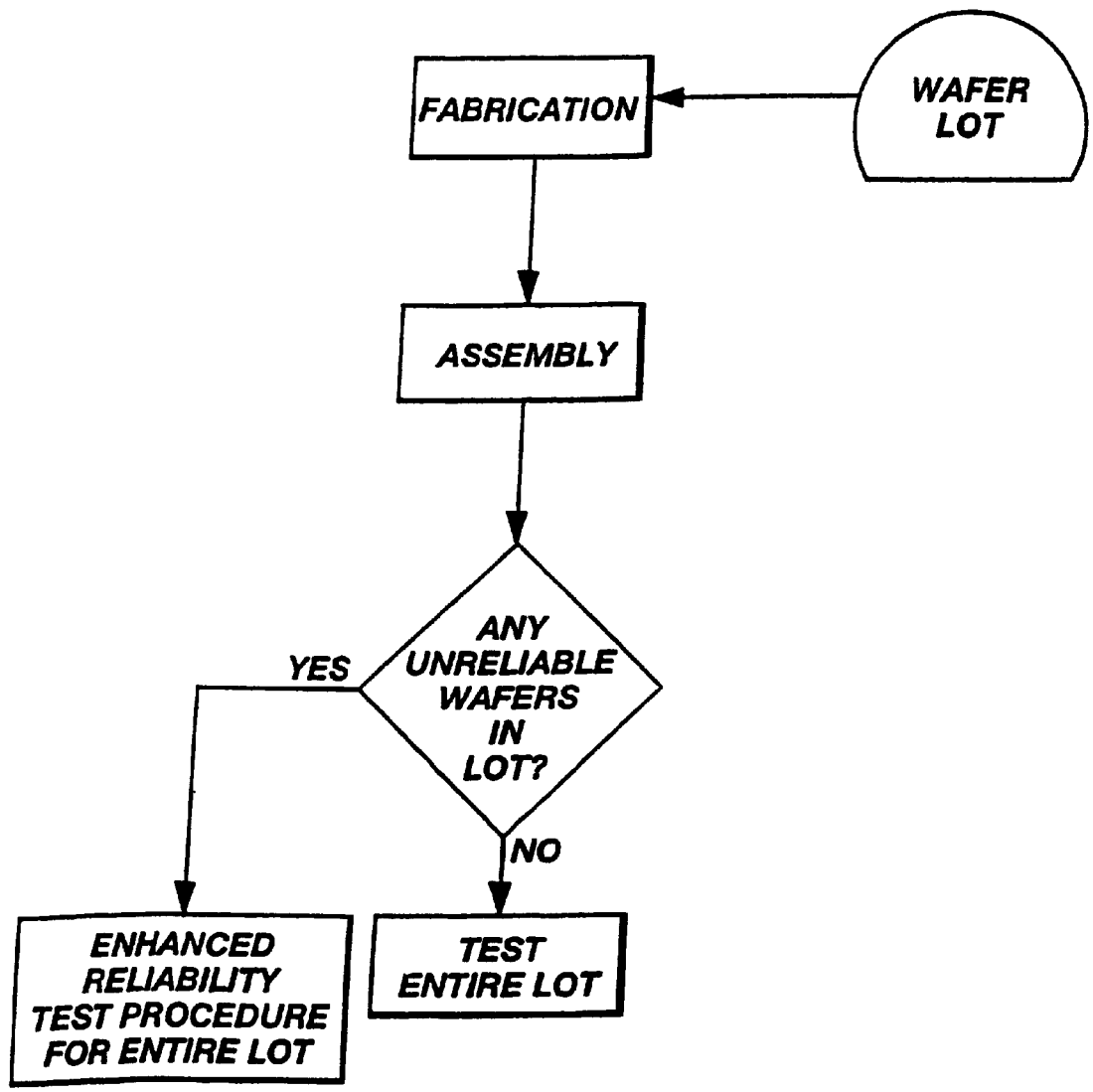
FIG. 2 is a flow diagram illustrating a conventional procedure in an IC manufacturing process for directing IC's to enhanced reliability testing.
Figure 3:
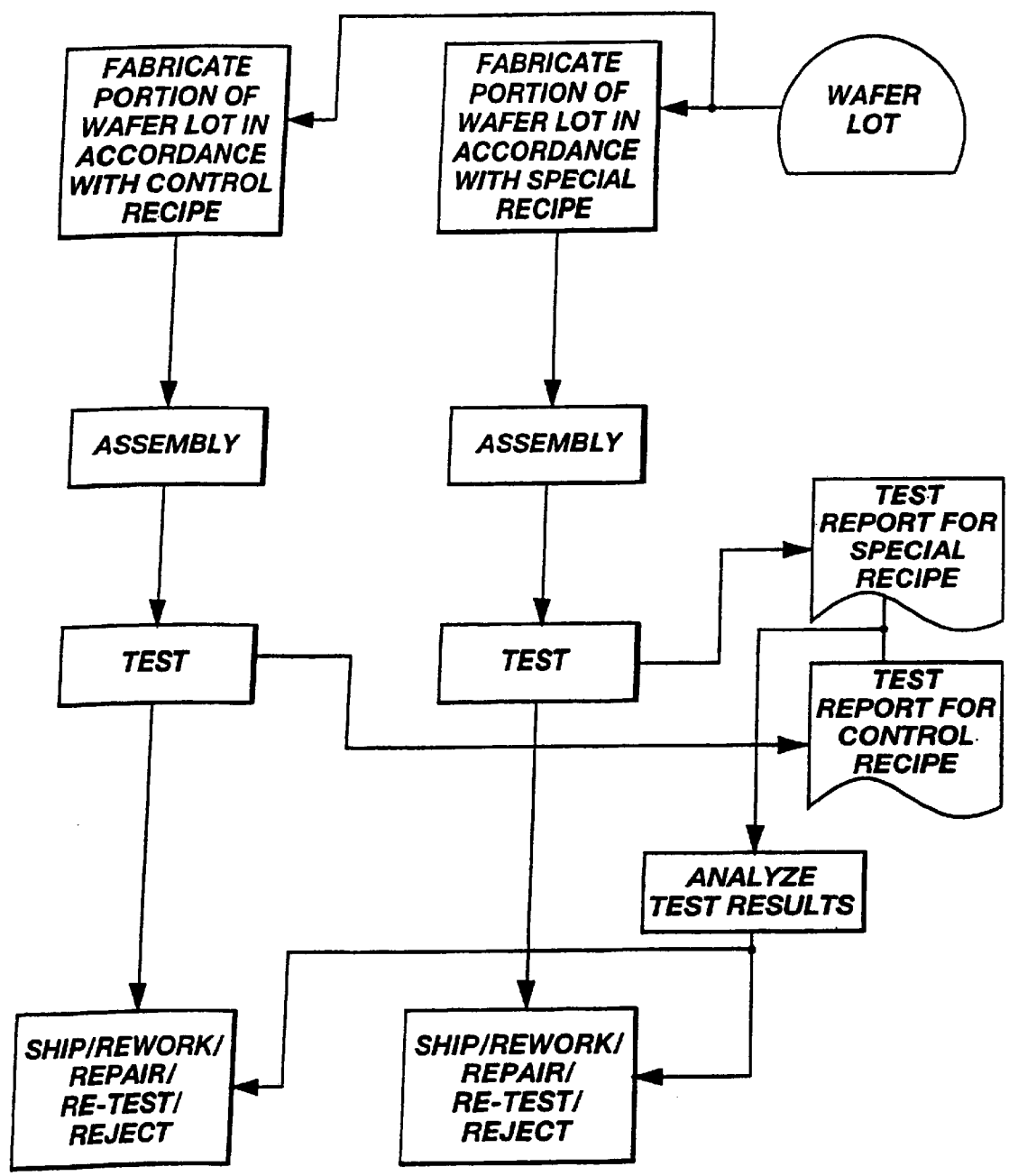
FIG. 3 is a flow diagram illustrating a conventional procedure in an IC manufacturing process for testing a new or special fabrication process recipe.
Figure 4:
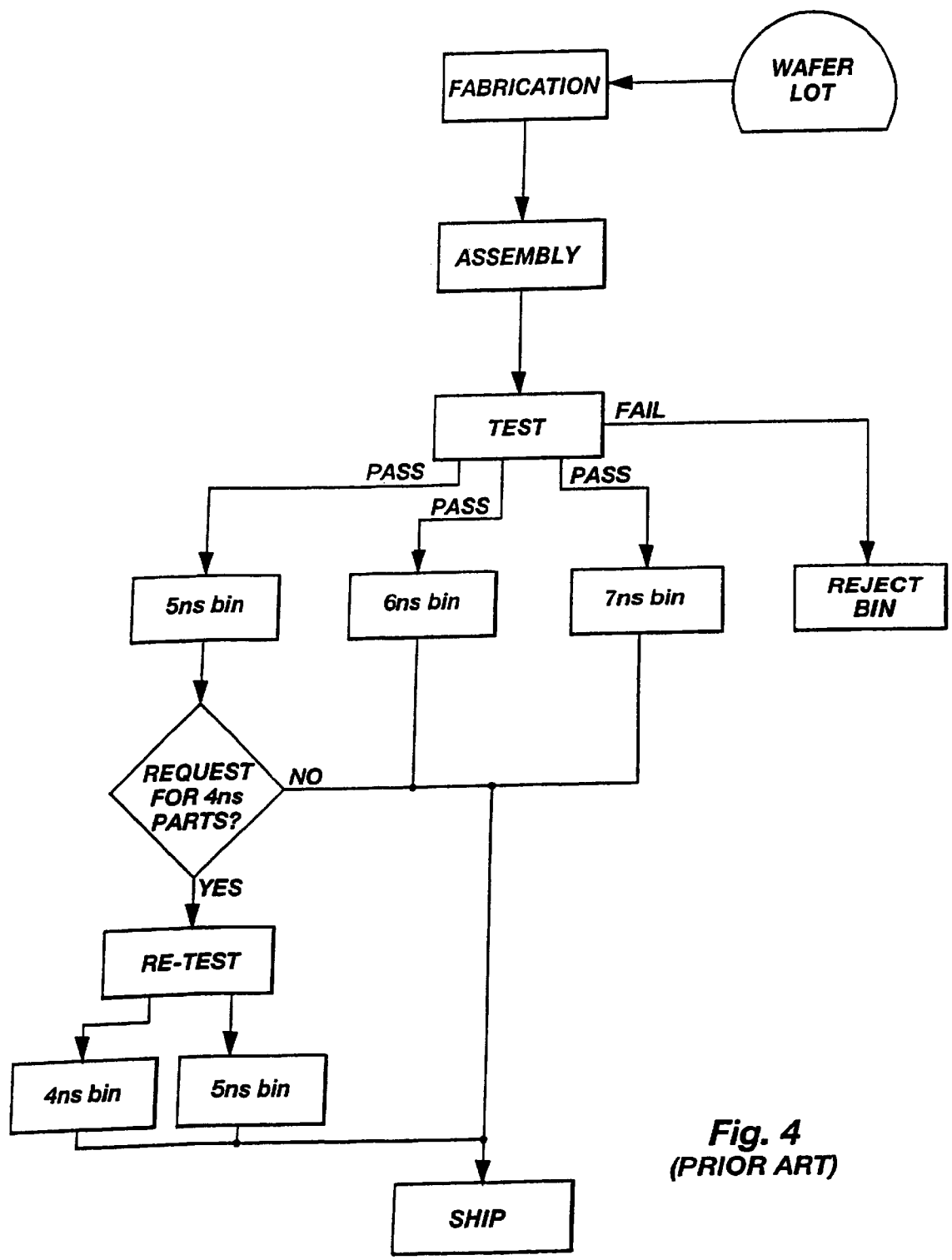
FIG. 4 is a flow diagram illustrating a conventional procedure in an IC manufacturing process for speed-sorting IC's.
Figure 5A:
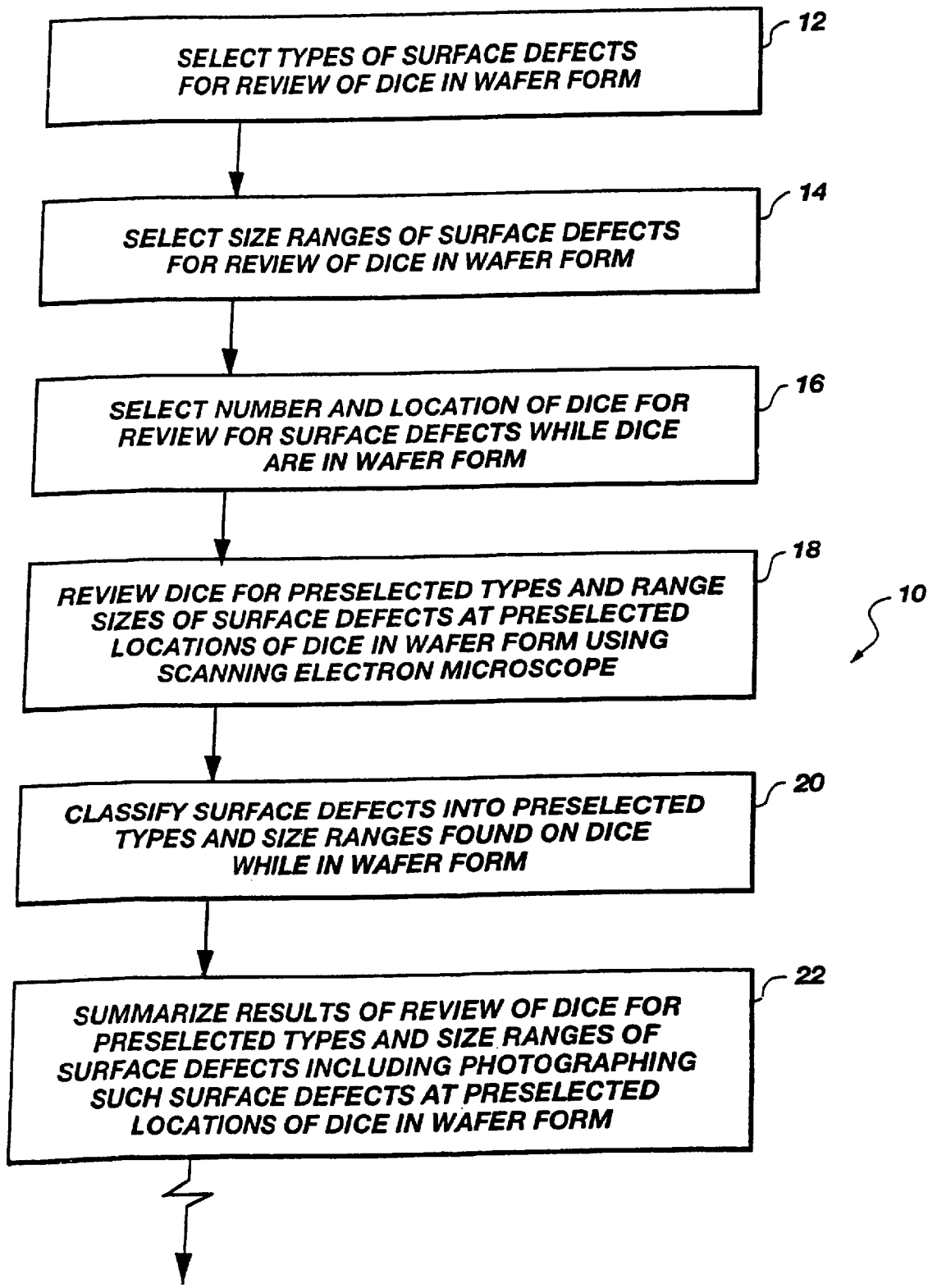
FIGS. 5A and 5B are a flow diagram illustrating the process of the present invention in an IC manufacturing process.
Figure 5B:
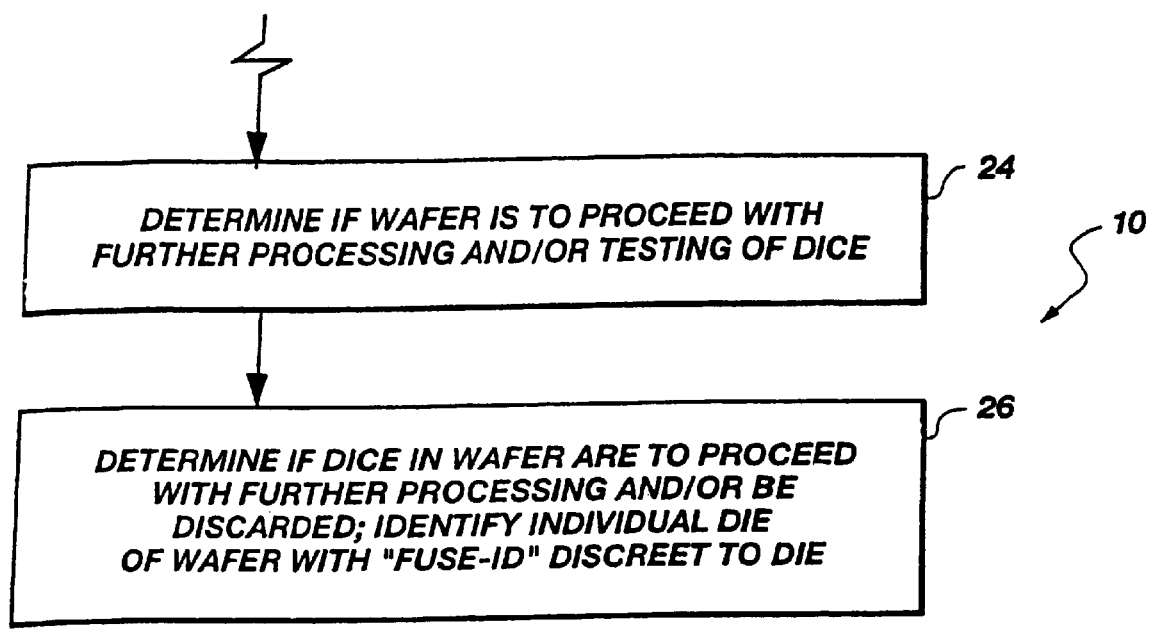

Referring to drawing FIGS. 5A and 5B, the flow diagram 10 illustrating the process of the present invention in an integrated circuit semiconductor device manufacturing process is set forth.

Referring to the step set forth in box 12 of the present invention, the types of surface defects in individual IC's located on the wafer to be discovered from a visual inspection of individual dice on the wafer are determined. Typically, the surface defects are to be visually determined using any commercially available automated defect detector for such purpose well known in the industry. Typical types of surface defects to be determined from a visual inspection of the dice of the wafer may include particle contamination of the dice from processing, bond pad formation problems, incomplete formation (scumming) of the circuits of the dice, etc., the types of visual defects being representative of those observed in normal IC processing in the wafer stage.

Referring to the next step of the method of the present invention set forth in box 14 of the drawings, the size ranges of the surface defects from the inspection of the dice of the wafer to be visually inspected are determined. For instance, surface defects present on the dice of the wafer are selected to be determined in size ranges for tabulation purposes, such as surface defects in the ranges of 0.0–0.5 microns, 0.5–1.0 microns, 1.0–1.5 microns, 1.5–2.0 microns, 2.0–4.0 microns, greater than 4.0 microns, etc.

Referring to step 16 of the present invention, the location of the dice to be inspected for surface defects thereon is determined with respect to the dice located on the wafer. That is, the surface defects are to be determined based upon either a predetermined method of selection of specific dice located in specific areas of the wafer under inspection based upon previous experience of various equipment in the manufacturing process tending to cause certain types of surface defects in die or dice in certain areas of the wafers or a random selection method of selecting dice randomly located throughout the wafer based upon statistical sampling techniques which are well known in the industry.

At this juncture in the present invention, it is clear that prior to the visual inspection of the dice of the wafer, (1) the types of surface defects to be determined by the visual inspection, (2) the location of the dice of the wafer to be visually inspected for surface defects thereon, and (3) the various size ranges of the types of surface defects to be determined from the visual inspection have been preselected prior to the visual inspection process of the dice of the wafer. Furthermore, it is preferred that each of these criteria is based upon historical information concerning the process of manufacture of the integrated circuit semiconductor device and any relationship present between the preselected criteria and subsequent failures of dice from a wafer during further processing, testing, and packaging of the dice. Such relationships may be determined by well known statistical analytical methods and data collected therefor used in the manufacturing of IC's.

Continuing, at the next step of the present invention set forth as step 18 of drawing FIGS. 5A and 5B, the preselected locations of dice on the wafer are visually inspected using any well known, commercially available scanning electron microscope or suitable optical microscope with tabulations of the resulting types of defects, frequency of defects, and sizes of defects being made through suitable means, such as by using a digital computer for such purposes. Also, preferably, a photograph may be made of each predetermined surface defect located on the dice of the wafer for comparison purposes with other defects of the same type classification and a record made of each surface defect and the location of the die containing such a defect on the wafer.

As shown in step 20 of the present invention, the surface defects of the preselected dice are classified, such being determined by the individual conducting the visual inspection as to the type of defect, the relative defect size, and the range of defect size into which such surface defect is to be classified as identified by the individual from the visual inspection of predetermined dice of the wafer.

After the visual inspection of the dice of the wafer, referring to step 22 of the present invention, the results of the visual inspection process are summarized. Typically, the results of the visual inspection are summarized in a tabular format according to defect type, description of the defect type, total for each defect type, and size range for such surface defect, and are also summarized in a wafer map illustrating such information in a graphical display of the dice of the wafer and defects discovered during the visual inspection of the dice of the wafer. An example of the tabular display 100 of surface defect information is illustrated in drawing FIG. 6, while the graphical screen display 200 of the dice of the wafer having surface deflects thereon is illustrated in drawing FIG. 7. While generated by summarizing the surface defect data using a digital computer for such purposes, it is preferred that the screen display 200 from the computer be printed out with subsequent information added by an individual as illustrated by marks 202 thereon for a record of the visual inspection results of the dice of the wafer.

At this time, referring to step 24 of the present invention, a determination is made as to whether the wafer is to proceed for further processing, testing, singulation of the dice, and/or packaging of the dice. In the first instance, a determination is made based upon the number of visual surface defects, types of visual surface defects of the dice, size of visual surface defects of the dice, the location of the visual surface defects of the dice with respect to the wafer and other dice of the wafer, etc. Such a determination is based upon information of previous wafers having visual surface defects of such determined size in such dice and the well known statistical analysis of such information from a reliability life history of such dice through well known statistical analysis techniques in the industry. Alternately, a determination may be made with respect to individual dice of the wafer as to subsequent processing by individually identifying each die through the use of electrically retrievable ID codes, such as so-called "fuse-ID's," programmed into individual IC's to identify the IC's. The programming of a fuse-ID typically involves selectively blowing an arrangement of fuses and anti-fuses in an IC so that when the fuses or anti-fuses are accessed, they output a selected ID code for each die unique to that die which may be readily determined during any subsequent processing through well known techniques hereinbefore set forth in the previously identified prior art patents which are incorporated herein by reference. In that manner, once the dice have been singulated from the wafer, the "fuse-ID" of each die may be determined and the desired subsequent processing, testing, and packaging determined, if any, with respect to individual dice believed to have reliability or functionality defects from the identification of visual surface defects while the dice are in the wafer stage prior to any testing thereof based upon known historical statistical information from such dice.

From the foregoing it can be easily recognized that through the use of only the screen display 200 of the wafer and the tabular display 100, the individual reviewing the wafer has permanent record of the information relating to the population of the visual defects of the dice of the wafer, the size of the defects, the types of visual defects, and, if desired, a pictorial record of the defect illustrating the same and how such defect relates to defects classified the same on the tabular display 100 and screen display 200. It should be clearly understood that the tabular display 100 not only provides a summary of the defect types, general defect description, and number of defects, as set forth in table 102, but also provides a histogram of such defect information, as set forth in table 104, which sets forth the identification of the die on the wafer (for instance, ID 329), the class of the defect (for instance, CL 3), and such information summarized in a tabular format, in the size range of the defect (for instance, 0.0–0.5 microns, 0.5–1 microns, 1–2 microns, 2–4 microns, etc.). In this manner, in a histogram format, such defect information is available and summarized for a wafer which has been inspected for defects. Also, the defect information contained within tables 102 and 104 has been inter-related or combined for wafer defect evaluation purposes. At such time, the further testing, processing, and packaging of the wafer and dice thereon may be determined either individually with respect to the wafer which has been inspected or collectively with respect to other wafers in the same production lot as the wafer which has been visually inspected. Alternately, the same may be determined regarding individual dice which have been discretely identified through the use of a "fuse-ID" for further processing, testing, packaging and/or being discarded.

In this manner, prior to any subsequent testing, processing or packaging of any dice, a determination of the quality of the manufacture of the dice in the wafer may be made, thereby avoiding any unnecessary expense in manufacturing an IC from the wafer. This avoids unnecessary subsequent testing of dice as well as the packaging thereof which are known through statistical analysis to be likely defective. Also, the various processing apparatus and methods of process forming the dice on the wafer may be modified for other wafers in the manufacturing process to help eliminate defects thereon.

From the foregoing it can be seen to one of ordinary skill in the art that changes, additions, deletions, and modifications may be made to the present invention which are intended to fall within the scope of the claimed invention.

What is claimed is:

1. A defect review method for a plurality of wafers in a process, each wafer of the plurality of wafers having integrated circuit semiconductor dice thereon, each integrated circuit semiconductor die of said integrated circuit semiconductor dice having a plurality of circuits, said method comprising:

determining from historical information concerning at least one process of manufacture of integrated circuit semiconductor dice on wafers at least one relationship between at least one type of surface defect on a plurality of said integrated circuit semiconductor dice on said wafers, said at least one type of surface defect visible to a user visually inspecting said integrated circuit semiconductor dice on said wafers for a surface defect thereon and determining at least one subsequent failure of a plurality of dice having a surface defect thereon of said integrated circuit semiconductor dice on said wafers;

visually inspecting a plurality of dice of integrated circuit semiconductor dice on a wafer to determine surface defects thereon by a user viewing said plurality of dice of said integrated circuit semiconductor dice on said wafer, said surface defects including at least one defect of defects from bond pad formation and from incomplete formation of said at least one plurality of circuits of each of said plurality of dice of said integrated circuit semiconductor dice on said wafer, said visually inspecting said plurality of dice of said integrated circuit semiconductor dice on said wafer including said user using one of a scanning electron microscope and an optical microscope;

selecting types of surface defects present on said plurality of dice of said integrated circuit semiconductor dice on said wafer from said visual inspection;

selecting a range of sizes of said surface defects from said visual inspection of said plurality of dice of said integrated circuit semiconductor dice on said wafer by said user;

selecting a number of said integrated circuit semiconductor dice for visual inspection on said wafer by said user selecting at least one other die of said integrated circuit semiconductor dice on said wafer for visual inspection thereof for surface defects thereon;

summarizing said number, types, and range of sizes of said surface defects of said plurality of dice and said at least one other die of said integrated circuit semiconductor dice on said wafer from a visual inspection of at least four dice of said integrated circuit semiconductor dice on said wafer by said user;

comparing said number, types and ranges of sizes of said surface defects of said plurality of dice and said at least one other die of said integrated circuit semiconductor dice on said wafer to said historical information concerning said at least one process of manufacture of integrated circuit semiconductor dice on wafers; and determining if said wafer is acceptable to proceed in said process of manufacture based upon said visual inspection of said at least four dice of said integrated circuit semiconductor dice on said wafer by said user and based upon said historical information concerning said at least one process of manufacture of integrated circuit semiconductor dice on wafers and said at least one relationship between said at least one type of surface defect on said plurality of dice of said integrated circuit semiconductor dice on said wafers visible to said user visually inspecting said integrated circuit semiconductor dice on said wafers and said at least one subsequent failure of said plurality of dice having said surface defect thereon of said integrated circuit semiconductor dice on said wafers.

2. A defect review process for integrated circuit semiconductor dice on a wafer in a process for said integrated circuit semiconductor dice, each integrated circuit semiconductor die of said integrated circuit semiconductor dice having at least one circuit, said process comprising:

determining from historical information concerning a process for integrated circuit semiconductor dice on wafers at least one relationship between at least one type of surface defect on at least more than two dice of said integrated circuit semiconductor dice on said wafers, said at least one type of surface defect visible to a user visually inspecting said integrated circuit semiconductor dice on said wafers for at least one surface defect thereon and determining at least one subsequent failure of more than two dice having a surface defect thereon of said integrated circuit semiconductor dice on said wafers;

visually inspecting said integrated circuit semiconductor dice on said wafer to determine surface defects thereon by said user visually inspecting more than two dice of said integrated circuit semiconductor dice on said wafer, said surface defects including at least one defect of defects from bond pad formation and from incomplete formation of said at least one circuit of each of said more than two dice of said integrated circuit semiconductor dice on said wafer, said visually inspecting said more than two dice of said integrated circuit semiconductor dice on said wafer including said user using one of a scanning electron microscope and an optical microscope;

classifying visual surface defects on said integrated circuit semiconductor dice of said wafer as to type and range of size of surface defect by said user from a manual visual inspection of said more than two dice of said integrated circuit semiconductor dice on said wafer;

determining a number of sid surface defects on said integrated circuit semiconductor dice on said wafer;

selecting a range of sizes of said surface defects from said visual inspection of said more than two dice of said integrated circuit semiconductor dice on said wafer by said user;

selecting a number of said integrated circuit dice for visual inspection on said wafer by said user selecting at least one other die of said integrated circuit semiconductor dice on said wafer for visual inspection thereof for surface defects thereon;

summarizing said number, types, and range of sizes of said surface defects on said integrated circuit semiconductor dice on said wafer by said user from said visual inspection of said more than two dice of said integrated circuit semiconductor dice on said wafer;

comparing said number, types and ranges of sizes of said surface defects of said more than two dice and said at least one other die of said integrated circuit semiconductor dice on said wafer to said historical information concerning said process for integrated circuit semiconductor dice on wafers;

determining if said wafer is acceptable to proceed in said process from a visual inspection of more than three dice of said integrated circuit semiconductor dice on said wafer by said user and based upon said historical information concerning said process for integrated circuit semiconductor dice on wafers and said at least one relationship between said at least one type of surface defect on said at least two dice of said integrated circuit semiconductor dice on said wafers visible to said user visually inspecting said integrated circuit semiconductor dice on said wafers and said at least one subsequent failure of said at least one die having said surface defect thereon of said integrated circuit semiconductor dice on said wafers; and photographing said surface defects on said integrated circuit semiconductor dice of said wafer from said visual inspection of said more than two dice of said integrated circuit semiconductor dice on said wafer by said user.

3. The process of claim 2, further including:

classifying visual surface defects of said more than two dice of said integrated circuit semiconductor dice of said wafer as to size of said visual surface defect.

4. The process of claim 3, further including:

classifying said visual surface defects of said more than two dice of said integrated circuit semiconductor dice of said wafer as to a size range of said visual surface defect.

5. The process of claim 4, further including:

summarizing the number, types, and range of sizes of said visual surface defects of said more than two dice of said integrated circuit semiconductor dice on said wafer in a tabular manner.

6. The process of claim 5, further including:

summarizing the number, types, and range of sizes of said visual surface defects of said more than two dice of said integrated circuit semiconductor dice on said wafer in a display of said integrated circuit semiconductor dice of said wafer.

7. The process of claim 2, further including:

determining if said wafer is acceptable to proceed in said process as a wafer being processed with other wafers having dice thereon as a group of wafers in said process.

8. The process of claim 2, further including:

determining if an individual die of said more than two dice of said integrated circuit semiconductor dice of said wafer is acceptable to proceed in said process.

9. A defect review method for integrated circuit semiconductor dice on a wafer in a process for said integrated circuit semiconductor dice, each integrated circuit semiconductor die of said integrated circuit semiconductor dice having a plurality of circuits, said method comprising:

determining from historical information concerning a process for integrated circuit semiconductor dice on wafers at least one relationship between at least one type of surface defect on more than two dice of said integrated circuit semiconductor dice on said wafers, said at least one type of surface defect visible to a user visually inspecting said integrated circuit semiconductor dice on said wafers for at least one surface defect thereon and determining at least one subsequent failure of more than two dice having a surface defect thereon of said integrated circuit semiconductor dice on said wafers;

selecting types of surface defects to be determined from said visual inspection of said integrated circuit semiconductor dice on said wafer by said user visually inspecting said more than two dice of said integrated circuit semiconductor dice on said wafer, said surface defects including at least one defect of defects from bond pad formation and from incomplete formation of said plurality of circuits of each of said integrated circuit semiconductor dice;

selecting a range of sizes of said surface defects to be determined from said visual inspection of said integrated circuit semiconductor dice on said wafer by said user from said visual inspection of said more than two dice of said integrated circuit semiconductor dice on said wafer;

selecting a number of said integrated circuit semiconductor dice for visual inspection on said wafer by said user from said visual inspection of said more than two dice of said integrated circuit semiconductor dice on said wafer;

visually inspecting at least one other integrated circuit semiconductor die of said integrated circuit semiconductor dice on said wafer to determine surface defects thereon by said user, said visually inspecting said more than two dice of said integrated circuit semiconductor dice on said wafer including said user using one of a scanning electron microscope and an optical microscope;

summarizing number, types, and range of sizes of said surface defects of said integrated circuit semiconductor dice on said wafer by said user from a visual inspection of at least three dice of said integrated circuit semiconductor dice on said wafer;

comparing said number, types and range of sizes of said surface defects of said more than two dice and said at least one other die of said integrated circuit semiconductor dice on said wafer to said historical information concerning said process for integrated circuit semiconductor dice on wafers; and determining if said wafer is acceptable to proceed in said process from said visual inspection of said at least three dice of said integrated circuit semiconductor dice on said wafer and based upon said historical information concerning said process for integrated circuit semiconductor dice on wafers and said at least one relationship between said at least one type of surface defect on said more than two dice of said integrated circuit semiconductor dice on said wafers visible to said user visually inspecting said integrated circuit semiconductor dice on said wafers and said at least one subsequent failure of said more than two dice having said surface defect thereon of said integrated circuit semiconductor dice on said wafers.

10. A method for processing of wafers having at least one integrated circuit semiconductor die thereon for determining defects in a process for said wafers, said at least one integrated circuit semiconductor die having a plurality of circuits, said method comprising:

determining from historical information concerning a process for integrated circuit semiconductor dice on wafers at least one relationship between at least one type of surface defect on more than two dice of said integrated circuit semiconductor dice on said wafers, the at least one type of surface defect visible to a user visually inspecting said integrated circuit semiconductor dice on said wafers for at least one surface defect thereon and determining at least one subsequent failure of more than two dice having a surface defect thereon of said integrated circuit semiconductor dice on said wafers;

selecting types of surface defects to be determined from a visual inspection of said integrated circuit semiconductor dice on said wafer by said user visually inspecting more than two dice of said integrated circuit semiconductor dice on said wafer, said types of surface defects including at least one surface defect of surface defects from bond pad formation and defects from incomplete formation of said plurality of circuits of said each integrated circuit semiconductor die of said integrated circuit semiconductor dice on said wafer;

selecting a range of sizes of said surface defects to be determined from said visual inspection of said integrated circuit semiconductor dice on said wafer by said user from said visual inspection of said more than two dice of said integrated circuit semiconductor dice on said wafer;

selecting a number of said integrated circuit semiconductor dice for visual inspection on said wafer by said user from said visual inspection of said more than two dice of said integrated circuit semiconductor dice on said wafer;

visually inspecting said integrated circuit semiconductor dice on said wafer to determine surface defects thereon by said user visually inspecting said more than two dice of said integrated circuit semiconductor dice on said wafer, wherein said visual inspection of said more than two dice of said integrated circuit semiconductor dice on said wafer includes using an apparatus for viewing said integrated circuit semiconductor dice;

summarizing number, types, and range of sizes of said surface defects of said integrated circuit semiconductor dice on said wafer by said user from said visual inspection of said more than two dice of said integrated circuit semiconductor dice on said wafer;

comparing said number, types and range of sizes of said surface defects of said more than two dice and at least one other die of said integrated circuit semiconductor dice on said wafer to said historical information concerning said process for said integrated circuit semiconductor dice on wafers; and determining if said wafer is acceptable to proceed in said process based upon said visual inspection by said user of said more than two dice on said wafer and based upon said historical information concerning said process for integrated circuit semiconductor dice on wafers and said at least one relationship between the at least one type of surface defect on said more than two dice of said integrated circuit semiconductor dice on the wafers visible to the user visually inspecting the integrated circuit semiconductor dice on said wafers and the at least one subsequent failure of said more than two dice having said surface defect thereon of said integrated circuit semiconductor dice on said wafers.

11. A method of determining defects for integrated circuit semiconductor dice on a wafer in a process for said integrated circuit semiconductor dice by a user, each integrated circuit semiconductor die of said integrated circuit semiconductor dice having a plurality of circuits, said method comprising:

determining from information concerning a process of manufacture of integrated circuit semiconductor dice on wafers relationships between at least two types of surface defects on at least two dice of said integrated circuit semiconductor dice on said wafers, said at least two types of surface defects visible to a user visually inspecting said integrated circuit semiconductor dice on said wafers for said at least two types of surface defects thereon and determining at least one subsequent failure of at least one die having a surface defect thereon of said integrated circuit semiconductor dice on said wafers;

selecting types of surface defects to be determined from a visual inspection of said integrated circuit semiconductor dice on said wafer by said user visually inspecting more than two dice of said integrated circuit semiconductor dice on said wafer, said surface defects including at least one surface defect of surface defects from bond pad formation and from incomplete formation of said plurality of circuits of said each integrated circuit semiconductor die of said integrated circuit semiconductor dice on said wafer, said visual inspection of said more than two dice of said integrated circuit semiconductor dice on said wafer including said user using one of a scanning electron microscope and an optical microscope;

selecting a size of said surface defects to be determined from said visual inspection of said integrated circuit semiconductor dice on said wafer by said user visually inspecting said more than two dice of said integrated circuit semiconductor dice on said wafer;

selecting a number of said integrated circuit semiconductor dice for visual inspection on said wafer by said user based on said visual inspection of said more than two dice of said integrated circuit semiconductor dice on said wafer;

visually inspecting at least one other die of said integrated circuit semiconductor dice on said wafer to determine surface defects thereon by said user;

summarizing number, types, and size of said surface defects of said integrated circuit semiconductor dice on said wafer by said user from a visual inspection of at least three dice of said integrated circuit semiconductor dice on said wafer;

comparing said number, types and size of said surface defects of said more than two dice and said at least one other die of said integrated circuit semiconductor dice on said wafer to said historical information concerning said process of manufacture for said integrated circuit semiconductor dice on wafers;

determining if said wafer is acceptable to proceed in said process of manufacture from said visual inspection of said at least three dice of said integrated circuit semiconductor dice on said wafer and based upon said historical information concerning said process of manufacture for integrated circuit semiconductor dice on wafers and said relationships between said at least two types of surface defects on said more than two dice of said integrated circuit semiconductor dice on said wafers visible to said user visually inspecting said integrated circuit semiconductor dice on said wafers and said at least one subsequent failure of said at least one die having said surface defect thereon of said integrated circuit semiconductor dice on said wafers; and photographing said surface defects on said integrated circuit semiconductor dice of said wafer from said visual inspection by said user of said more than two dice of said integrated circuit semiconductor dice on said wafer.

12. The method of claim 11, further including:
classifying visual surface defects of said integrated circuit semiconductor dice of said wafer as to type of surface defect.

13. The method of claim 12, further including:
classifying said visual surface defects of said integrated circuit semiconductor dice of said wafer as to size of said visual surface defects.

14. The method of claim 13, further including:
classifying said visual surface defects of said integrated circuit semiconductor dice of said wafer as to a size range of said visual surface defects.

15. The method of claim 14, further including:
summarizing said number, types, and range of sizes of said visual surface defects of said integrated circuit semiconductor dice on said wafer in a tabular manner.

16. The method of claim 15, further including:
summarizing said number, types, and range of sizes of said visual surface defects of said integrated circuit semiconductor dice on said wafer in a display of said integrated circuit semiconductor dice of said wafer.

17. The method of claim 11, further including:
determining if said wafer is acceptable to proceed in said process of manufacture as a wafer being processed with other wafers having integrated circuit semiconductor dice thereon as a group of wafers in said process of manufacture.

18. The method of claim 11, further including:
determining if an individual die of said integrated circuit semiconductor dice of said wafer is acceptable to proceed in said process of manufacture.

19. A method for determining defects of integrated circuit semiconductor dice on a wafer in a process for said integrated circuit semiconductor dice by a user, each integrated circuit semiconductor die of said integrated circuit semiconductor dice having a plurality of circuits, said method comprising:

determining from historical information concerning a process of manufacture of integrated circuit semiconductor dice on wafers at least one relationship between at least one type of surface defect on more than two integrated circuit semiconductor dice of said integrated circuit semiconductor dice on said wafers, said at least one type of surface defect visible to a user visually inspecting said integrated circuit semiconductor dice on said wafers for at least one surface defect thereon and determining at least one subsequent failure of at least one integrated circuit semiconductor die having a surface defect thereon of said integrated circuit semiconductor dice on said wafers, said visual inspection of said more than two dice of said integrated circuit semiconductor dice on said wafer by said user including said user operating one of a scanning electron microscope and an optical microscope;

visually inspecting more than two dice of said integrated circuit semiconductor dice on said wafer to determine surface defects thereon by said user, said surface defects including at least one surface defect of surface defects from bond pad formation and from incomplete formation of said plurality of circuits of said each integrated circuit semiconductor die of said integrated circuit semiconductor dice on said wafer, said surface defects having a type and size;

summarizing the surface defects on said integrated circuit semiconductor dice on said wafer by said user from said visual inspection of said more than two dice of said integrated circuit semiconductor dice on said wafer;

comparing number, types and ranges of sizes of said surface defects of at least one integrated circuit semiconductor die and at least one other integrated circuit semiconductor die of said integrated circuit semiconductor dice on said wafer to said historical information concerning said process of manufacture of integrated circuit semiconductor dice on wafers; and determining if said wafer is acceptable to proceed in said process of manufacture from said visual inspection of said more than two dice of said integrated circuit semiconductor dice on said wafer and based upon said historical information concerning said process of manufacture for integrated circuit semiconductor dice on wafers and said at least one relationship between said at least one type of surface defect on said more than two dice of said integrated circuit semiconductor dice on said wafers visible to said user visually inspecting said integrated circuit semiconductor dice on said wafers and said at least one subsequent failure of said at least two dice having said surface defect thereon of said integrated circuit semiconductor dice on said wafers.

20. The method of claim 19, further comprising:

selecting types of said surface defects to be determined from said visual inspection of said integrated circuit semiconductor dice on said wafer by said user from a visual inspection of at least three integrated circuit semiconductor dice of said integrated circuit semiconductor dice on said wafer;

selecting sizes of said surface defects to be determined from said visual inspection of said at least three integrated circuit semiconductor dice of said integrated circuit semiconductor dice on said wafer; and selecting at least three of said integrated circuit semiconductor dice for visual inspection on said wafer from said visual inspection of at least three dice of said integrated circuit semiconductor dice on said wafer.

21. The method of claim 19, wherein said visually inspecting said integrated circuit semiconductor dice on said wafer includes using a scanning electron microscope or optical microscope by said user.

* * * * *

UNITED STATES PATENT AND TRADEMARK OFFICE
CERTIFICATE OF CORRECTION

Figure 7:
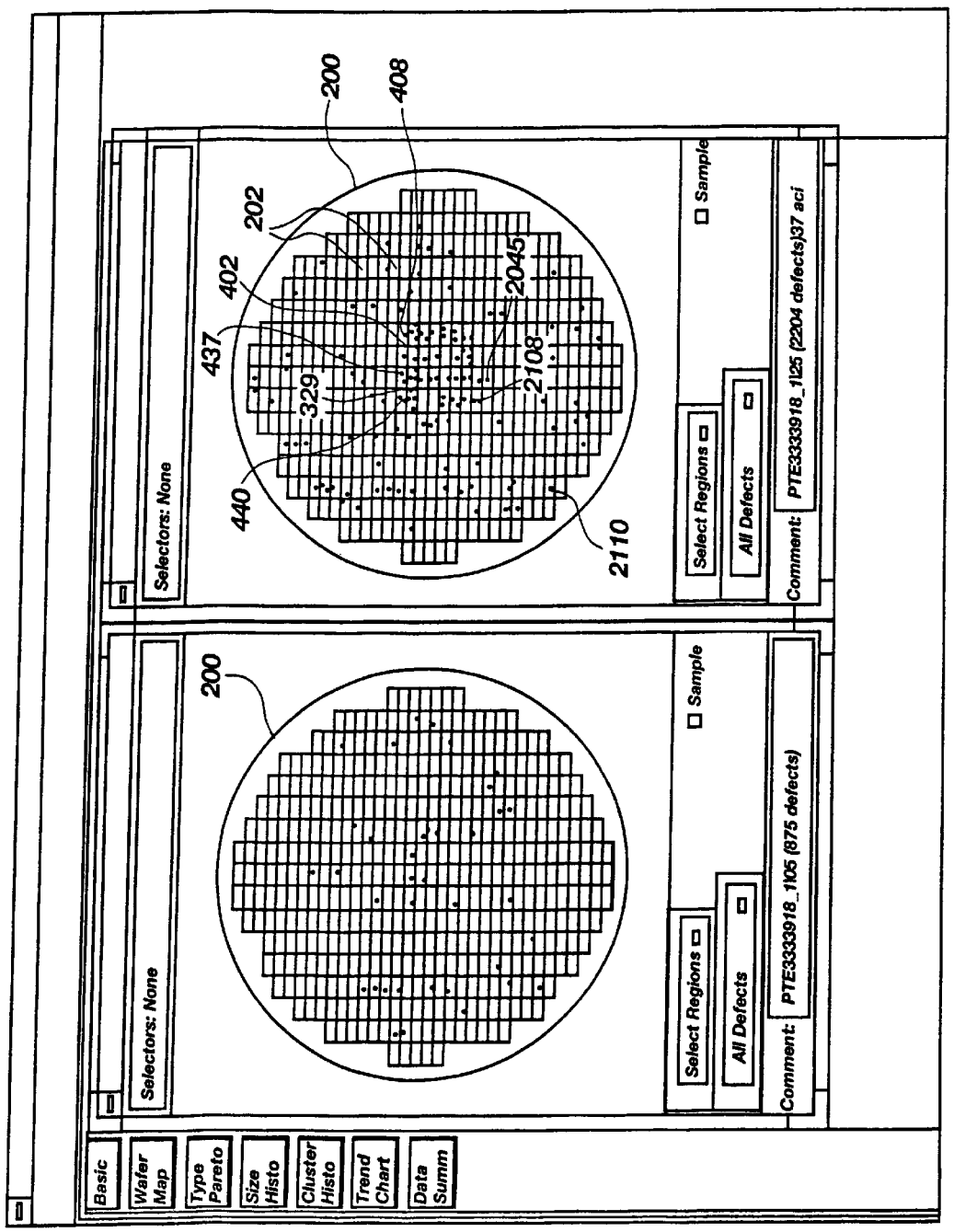
FIG. 7 is a graphical display of the dice of a wafer which has been inspected according to the present invention.
Figure 7:
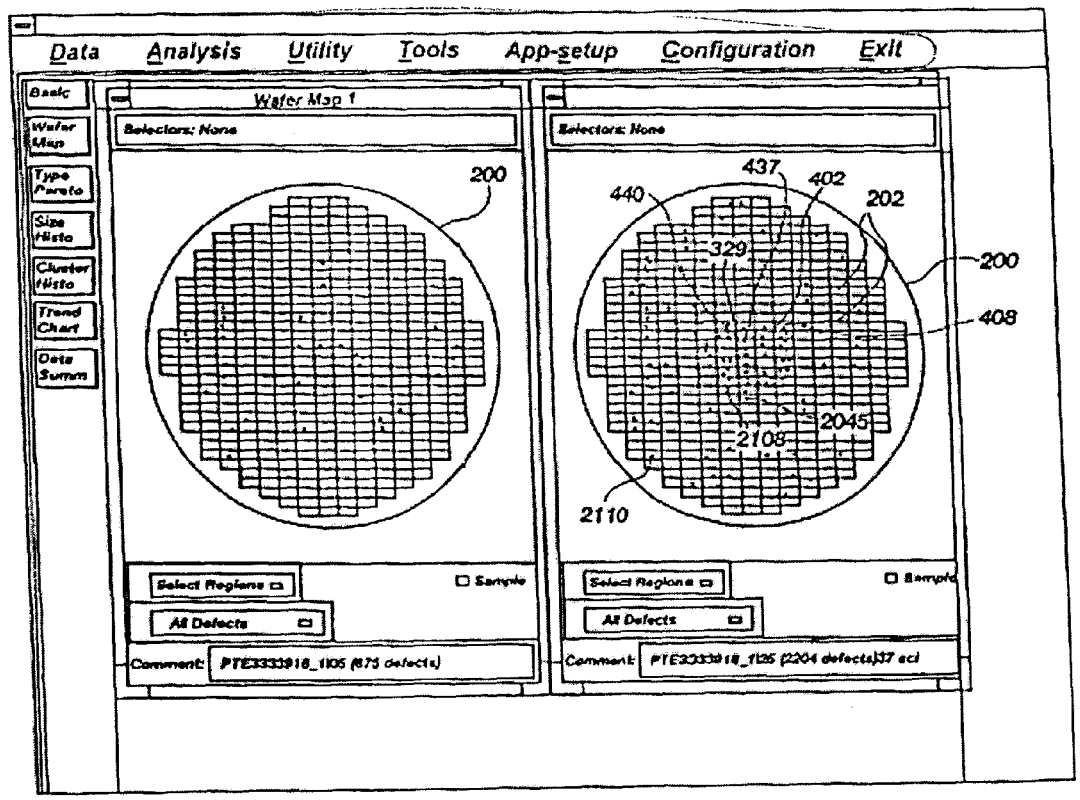

PATENT NO. : 6,654,114 B2
DATED : November 25, 2003
INVENTOR(S) : Lisa R. Zeimantz It is certified that error appears in the above-identified patent and that said Letters Patent is hereby corrected as shown below:

Delete drawing sheet 8 consisting of Fig. 7, and substitute therefor Drawing Sheet 8 consisting of Fig. 7, as shown on attached sheet.

Column 5,
Line 2, change "deflects" to -- defects --

Column 7,
Line 63, change "sid" to -- said --

Signed and Sealed this

Fourteenth Day of September, 2004

JON W. DUDAS
*Director of the United States Patent and Trademark Office*